US010315964B2

(12) United States Patent
Lim et al.

(10) Patent No.: US 10,315,964 B2
(45) Date of Patent: Jun. 11, 2019

(54) METHOD FOR MARKING OIL PRODUCTS AND MARKER COMPOSITION FOR OIL PRODUCTS

(71) Applicant: KOREA INSTITUTE OF PETROLEUM MANAGEMENT, Seongnam-si, Gyeonggi-do (KR)

(72) Inventors: Young-Kwan Lim, Suwon-si (KR); Hee-Yeon Baek, Seongnam-si (KR); Kyoung-Heum Lee, Yongin-si (KR); Seung-Hyun Ryu, Yongin-si (KR); Ju Min Youn, Daejeon (KR); Jong Ryeol Kim, Yongin-si (KR); In Ha Hwang, Suwon-si (KR); Jong Han Ha, Hwaseong-si (KR)

(73) Assignee: Korea Institute of Petroleum Management, Seongnam-si (KR)

( * ) Notice: Subject to any disclaimer, the term of this patent is extended or adjusted under 35 U.S.C. 154(b) by 36 days.

(21) Appl. No.: 15/322,617

(22) PCT Filed: Nov. 9, 2016

(86) PCT No.: PCT/KR2016/012863
§ 371 (c)(1),
(2) Date: Dec. 28, 2016

(87) PCT Pub. No.: WO2017/086654
PCT Pub. Date: May 26, 2017

(65) Prior Publication Data
US 2017/0297971 A1    Oct. 19, 2017

(30) Foreign Application Priority Data
Nov. 20, 2015  (KR) ........................ 10-2015-0162923

(51) Int. Cl.
| C07C 1/12 | (2006.01) |
| C07B 59/00 | (2006.01) |
| C07C 11/02 | (2006.01) |
| C07C 15/44 | (2006.01) |
| G01N 30/72 | (2006.01) |
| C07C 9/21 | (2006.01) |
| G01N 24/08 | (2006.01) |
| C07C 9/15 | (2006.01) |
| C07C 13/20 | (2006.01) |
| G01N 33/28 | (2006.01) |
| G01N 30/88 | (2006.01) |

(52) U.S. Cl.
CPC .............. *C07B 59/001* (2013.01); *C07C 1/12* (2013.01); *C07C 9/15* (2013.01); *C07C 9/21* (2013.01); *C07C 11/02* (2013.01); *C07C 13/20* (2013.01); *C07C 15/44* (2013.01); *G01N 24/088* (2013.01); *G01N 30/72* (2013.01); *C07B 2200/05* (2013.01); *G01N 33/28* (2013.01); *G01N 2030/8854* (2013.01)

(58) Field of Classification Search
CPC ......... G01N 2030/025; G01N 33/2882; G01N 2030/8868; G01N 2030/8854; G01N 33/1826; G01N 33/28; G01N 2030/047; G01N 21/3577; G01N 21/359; G01N 21/65; G01N 24/08; G01N 24/088; G01N 30/468; G01N 30/72; G01N 30/7206; G01N 33/22; G01N 33/227; C07C 11/02; C07C 1/12; C07C 13/20; C07C 15/44; C07C 2601/14; C07C 2601/16; C07C 321/30; C07C 323/20; C07C 43/2055; C07C 43/21; C07C 43/263; C07C 43/275; C07C 9/15; C07C 9/21
See application file for complete search history.

(56) References Cited

U.S. PATENT DOCUMENTS

2005/0019939 A1* 1/2005 Spall .................... G01N 21/359
436/139

FOREIGN PATENT DOCUMENTS

| JP | H0894579 | 4/1996 |
| JP | H09257780 | 10/1997 |
| JP | 2005502760 | 1/2005 |
| JP | 2006023184 | 1/2006 |
| JP | 2011095170 | 5/2011 |
| KR | 20150025864 A | 3/2015 |

* cited by examiner

Primary Examiner — Sharon Pregler
(74) Attorney, Agent, or Firm — Hauptman Ham, LLP

(57) ABSTRACT

According to the present invention, a deuterium-substituted marker for fuel is synthesized through substitution with deuterium so as to have structurally and chemically similar properties to those of a molecule configuring fuel oil. A molecule of the deuterium-substituted marker is significantly similar to the conventional molecule configuring the fuel oil, which may prevent illegal removal of the marker by the fake oil manufacturers. According to the present invention, it is able to pursue public safety and environmental protection from fake oil products, and to prevent national tax evasion, by preventing the illegal mixing of fuel oil to secure a legal distribution of the oil market according to the present invention.

1 Claim, 4 Drawing Sheets

METHOD FOR MARKING OIL PRODUCTS AND MARKER COMPOSITION FOR OIL PRODUCTS

TECHNICAL FIELD

The present invention relates to a method for marking oil products using a novel form of a marker for oil products which is not easily removable by physical and chemical methods and is able to easily determine whether illegal mixing of the oil products occurs, and a marker composition for oil products used for the method.

BACKGROUND ART

A marker and a dye are mixed in a fuel to be used for classification of oil types of liquid fuel products, taxable products and tax-free products, and for prevention of illegal incorporation and manufacture all over the world. The marker is diluted in the oil products at a low concentration (10 to 200 mg/kg) in order not to change physical properties of the fuel, and has a stable structure in which chemical reactions are not generated by a fuel component itself.

The marker used in a petrochemical industry is largely divided into a visible marker, a covert marker, and a chemical marker. The visible marker is advantageous in view of price, but is disadvantageous in that it is easy to be illegally removed, and the covert marker is difficult to be illegally removed, but has disadvantages in that it requires a high-priced specific analysis equipment, and the price is expensive. Accordingly, a number of countries largely use the chemical marker having the advantage while compensating the disadvantages of both of the markers. The chemical marker generates the chemical reaction with a developer to visualize a specific color, and is used to classify the oil types and to prevent the illegal incorporation into high-priced products or into taxable products by mixing the chemical marker with specific oil (non-taxable products or low-priced oil types, etc.) at a predetermined ratio. Accordingly, in order to determine whether the illegal incorporation occurs, the developer has added a marker that shows up as a color, and whether the marker is present is determined by using a UV-Vis spectrophotometer.

Meanwhile, there are a number of cases that low-priced oil products are illegally mixed with other high-priced oil products and distributed by fake oil manufacturers. In particular, kerosene is illegally mixed with automotive diesel to manufacture fake diesel. Now, the chemical marker included in the kerosene has a disadvantage in that it is easy to be illegally removed, which is difficult to exactly determine whether other products are illegally mixed with normal oil products. Cases where the kerosene is illegally mixed with the diesel to be distributed by using this disadvantage, have arisen. In addition, the manufactured fake diesel has low quality standards as compared to normal diesel, and reduced output in high engine revolution by 2 to 3%. In addition, when measuring exhaust gas, emissions such as carbon monoxide (CO), nitrogen oxide (NOx), unburned hydrocarbon (THC), etc., are increased by up to about 20%, air pollution is induced, and at the same time, a large-scale accident resulting from breakdown of car components such as a fuel injector, a fuel pump, etc., due to a decrease in lubricity may be caused.

That is, the fake oil manufactured by the illegal mixing of fuel oil causes a national tax evasion problem, a safety problem due to vehicle breakdown by owners, and an environmental pollution problem resulting from an increase in emission gases, etc. In order to prevent the illegal mixing of the fuel oil, the marker corresponding to oil types is incorporated to be distributed, but the conventionally developed marker for fuel has most of the artificial molecules that are not included in the fuel component, the molecule having large molecular weight and polar characteristic as compared to molecules forming the fuel, such that the marker in the fuel may be illegally removed by various removing methods suitable for properties of the marker.

Therefore, a novel form of a marker for oil products which is not easily removable by physical and chemical methods and is able to easily determine whether illegal mixing of the oil products occurs, has been demanded.

RELATED ART DOCUMENT (Patent Document) Korean Patent Laid-Open Publication No. KR 2015-0025864

DISCLOSURE OF INVENTION

Technical Problem

The present inventors made an effort to develop a marker in which hydrogen in hydrocarbons that are fuel components is substituted with deuterium, wherein since a change in molecular weight and a polarity degree are not large, it is not possible to easily perform illegal removal of the marker which is unlike the conventionally developed marker, such that illegal mixing of fuel may be prevented.

In addition, whether there is a marker for fuel substituted with deuterium may be easily determined by using nuclear magnetic resonance (NMR), gas chromatography-Mass (GC-MS), etc., such that the illegal mixing of oil types may be easily exposed.

Specifically, an object of the present invention is to provide a method for labeling oil products using a marker for oil products including hydrocarbon substituted with at least one deuterium and for marking various oil products through nuclear magnetic resonance spectroscopy or gas chromatography-mass spectrometry.

Another object of the present invention is to provide a marker composition for oil products including hydrocarbon substituted with at least one deuterium.

Still another object of the present invention is to pursue public safety and environmental protection from fake oil products, and to prevent national tax evasion, by preventing the illegal mixing of fuel oil to secure healthy distribution order of oil market.

Solution to Problem

The present invention relates to a method for marking oil products using a novel form of a marker for oil products which is not easily removable by physical and chemical methods and is able to easily determine whether illegal mixing of the oil products occurs, and a marker composition for oil products used for the method.

In one general aspect, there is provided a method for marking oil products including: measuring a nuclear magnetic resonance spectrum or a gas chromatography mass analysis spectrum of an oil product labeled with a marker for oil products, the marker including hydrocarbon substituted with at least one deuterium.

The hydrocarbon may be one or more selected from C1-C30 saturated hydrocarbon substituted with at least one deuterium, C5-C30 aromatic hydrocarbon substituted with at least one deuterium, and C2-C30 unsaturated hydrocarbon substituted with at least one deuterium.

The hydrocarbon may be substituted with 1 to 50 deuteriums.

The saturated hydrocarbon may be a chain type, a branched type or a cyclic type.

The deuterium may be substituted inside of the hydrocarbon or at the end of the hydrocarbon.

The C1-C30 saturated hydrocarbon substituted with at least one deuterium may be selected from structures below, but is not limited thereto:

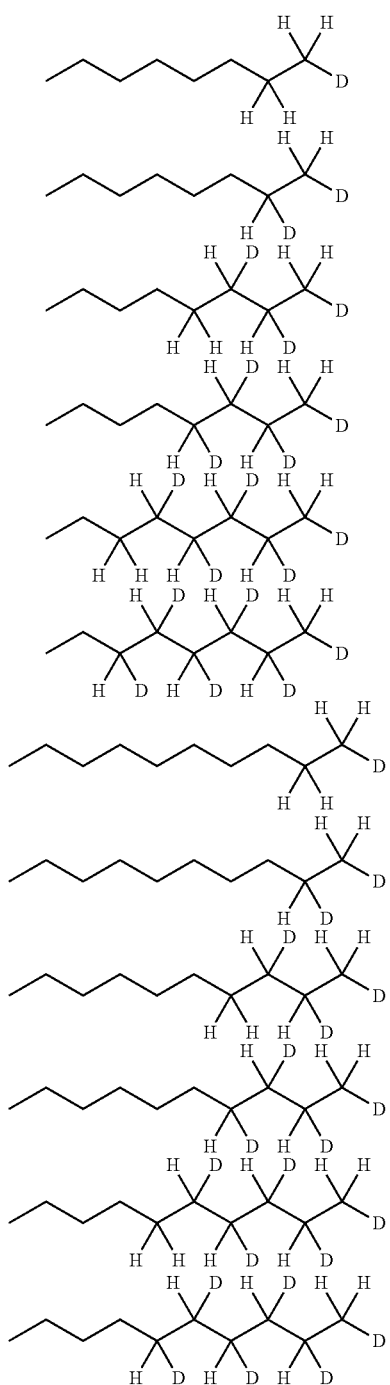

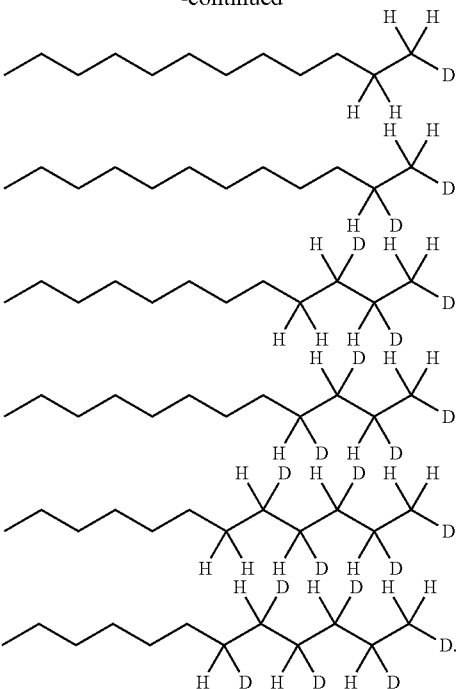

The saturated hydrocarbon substituted with at least one deuterium may be C5-C30 cyclic hydrocarbon substituted with at least one deuterium.

The C5-C30 aromatic hydrocarbon substituted with at least one deuterium may be selected from benzene substituted with 1 to 6 deuteriums, naphthalene substituted with 1 to 8 deuteriums, toluene substituted with 1 to 8 deuteriums, and xylene substituted with 1 to 10 deuteriums, but is not limited thereto.

The C2-C30 unsaturated hydrocarbon substituted with at least one deuterium may be selected from structures below, but is not limited thereto:

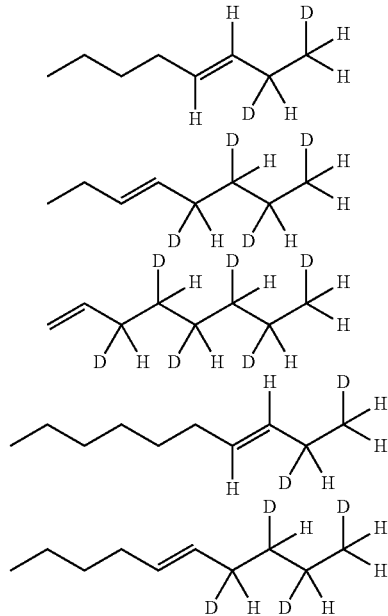

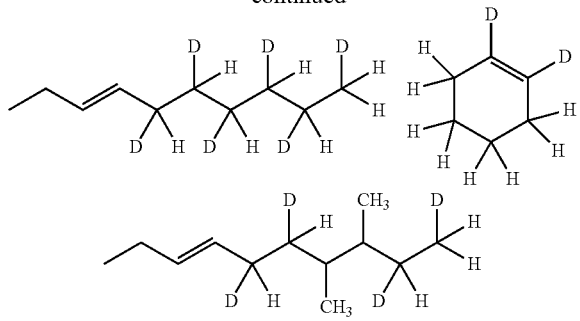

In another general aspect, there is provided a marker composition for oil products including hydrocarbon substituted with at least one deuterium.

The hydrocarbon may be one or more selected from C1-C30 saturated hydrocarbon substituted with at least one deuterium, C5-C30 aromatic hydrocarbon substituted with at least one deuterium, and C2-C30 unsaturated hydrocarbon substituted with at least one deuterium.

The marker composition for oil products may further include a chemical marker, a visible marker, or a mixture thereof.

The chemical marker may be Unimark 1494DB, and the visible marker may be one or two or more selected from MAXOL RED-4L, GREENER, MAXOL BLUE-4L, MAXOL BLACK, etc.

Advantageous Effects of Invention

The present invention provides a novel form of a marker for oil products which is not easily removable by physical and chemical methods and is able to easily determine whether illegal mixing of the oil products occurs, which is able to easily determine whether illegal incorporation of the fuel occurs, by labeling oil products with the marker using hydrocarbon substituted with at least one deuterium, and by determining whether the deuterium-substituted marker for fuel is contained by nuclear magnetic resonance spectroscopy or gas chromatography mass spectrometry.

In addition, the marker for oil products according to the present invention has a structure in which hydrogen of the conventional oil components is substituted with deuterium, wherein a change in molecular weight and a polarity degree are not large. The marker for oil products has high solubility in oil fuels, and a liquid form, and neither has colors nor has a change in a fuel shape even if the marker is added to the oil fuels. Accordingly, the illegal removal of the marker is virtually impossible due to physical and chemical similarity with the conventional oil components.

MODE FOR THE INVENTION

Figure 1:
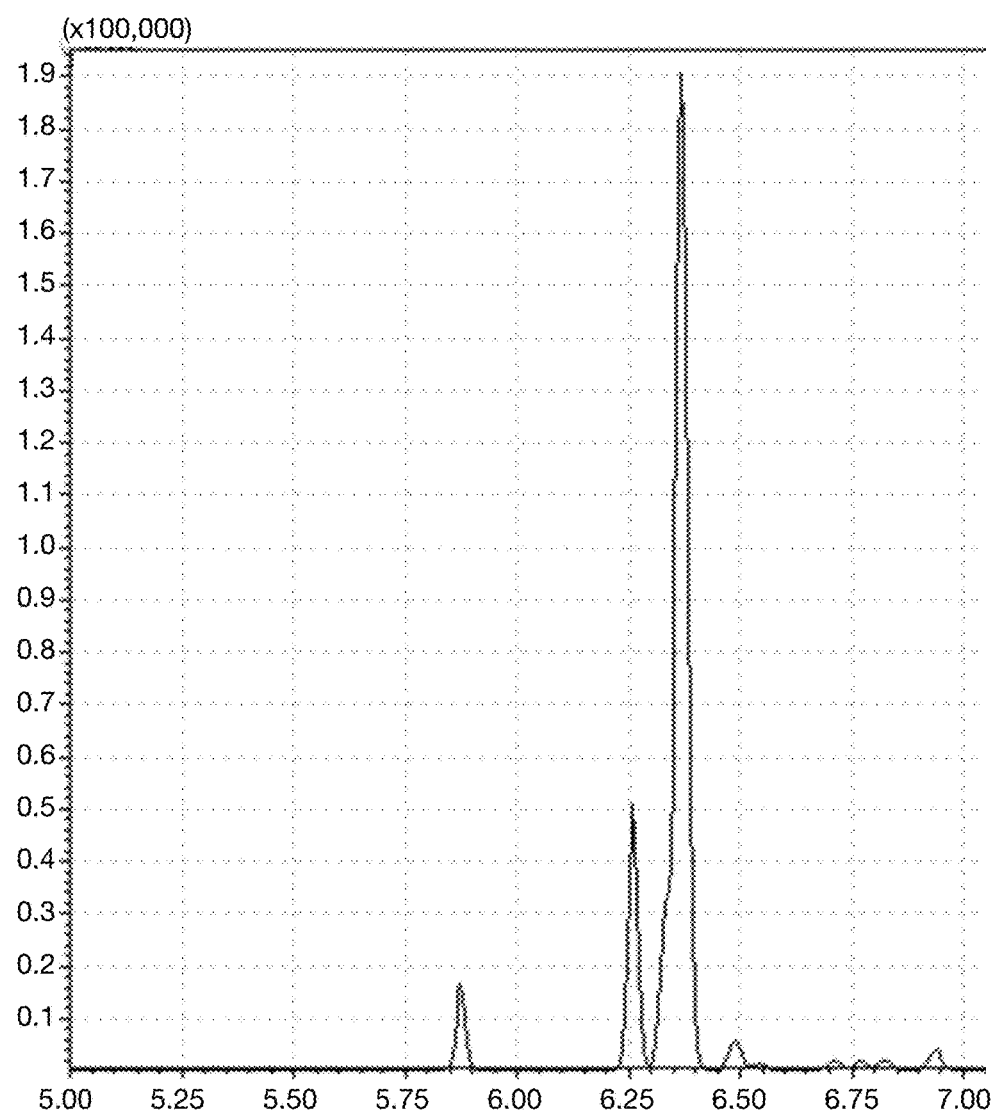
FIG. 1 illustrates GC-MS spectrum of benzene D-6 ($C_6D_6$) which is a marker included in kerosene.

The present invention relates to a method for marking oil products using a novel form of a marker for oil products which is not easily removable by physical and chemical methods and is able to easily determine whether illegal mixing of the oil products occurs, and a marker composition for oil products used for the method. More specifically, the present invention relates to the method for marking oil products using the marker for fuel in which whether illegal mixing of the fuel occurs is easily determined, and it is difficult to perform artificial illegal removal of the marker, by artificially substituting deuterium in hydrocarbon which is oil component molecules, the deuterium having a very low natural abundance ratio, and a marker composition for oil products used for the method.

The present invention provides a method for marking oil products including: measuring a nuclear magnetic resonance spectroscopy or a gas chromatography mass analysis spectrum of an oil product labeled with a marker for oil products, the marker including hydrocarbon substituted with at least one deuterium.

The present invention provides a novel form of a marker for oil products which is not easily removable by physical and chemical methods and is able to easily determine whether illegal mixing of the oil products occurs, which uses hydrocarbon substituted with at least one deuterium, and the oil products labeled by the marker is able to enhance a field crackdown capacity on illegal oil products by a simple confirmation through the nuclear magnetic resonance spectroscopy or the gas chromatography mass analysis spectrometry, such that it is possible to protect high quality oil products, and to prevent exhaust gas pollution, which contributes to the protection of atmospheric environment, and allow consumers to use the high quality oil products with an easy mind. Further, it is possible to contribute to recovery of reliability of oil product market, and further, the high quality of oil products may be used to protect automobile engine using petroleum, which makes it possible to use the automobile for a long period of time. Accordingly, it is able to pursue public safety and environmental protection from fake oil products, and to prevent national tax evasion, by preventing the illegal mixing of fuel oil to secure healthy distribution order of oil market according to the present invention.

In an exemplary embodiment of the present invention, the hydrocarbon is one or more selected from C1-C30 saturated hydrocarbon substituted with at least one deuterium, C5-C30 aromatic hydrocarbon substituted with at least one deuterium, and C2-C30 unsaturated hydrocarbon substituted with at least one deuterium, wherein the hydrocarbon may be substituted with 1 to 50 deuteriums, and the deuterium may be substituted inside of the hydrocarbon or at the end of the hydrocarbon.

In an exemplary embodiment of the present invention, the hydrocarbon may be mixed in the oil products at a concentration of 1 ppb to 1000 ppm, When the concentration is out of the above-described range, a detection sensitivity may be reduced.

In addition, in an exemplary embodiment of the present invention, the saturated hydrocarbon is a chain type or a branched type, and specifically exemplified with structures below, but is not limited thereto:

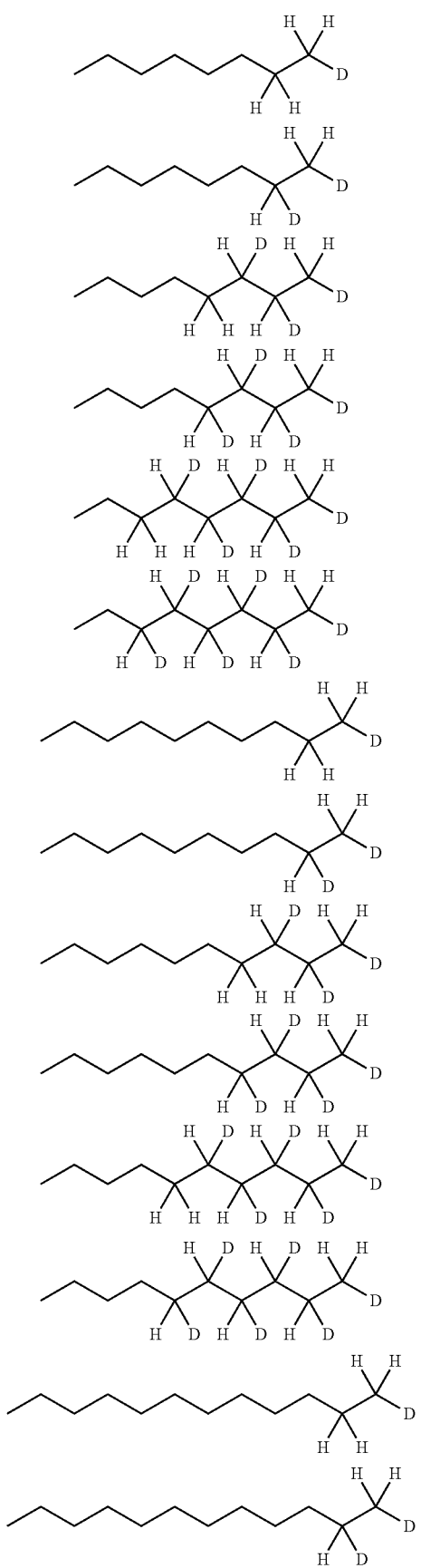

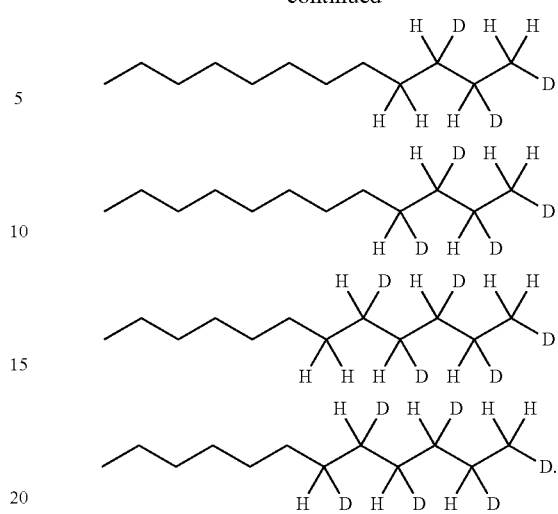

Further, in an exemplary embodiment of the present invention, the saturated hydrocarbon is a cyclic type, and may be C5-C30 cyclic hydrocarbon substituted with at least one deuterium.

In addition, in an exemplary embodiment of the present invention, the C5-C30 aromatic hydrocarbon substituted with at least one deuterium may be, for example, benzene substituted with 1 to 6 deuteriums, naphthalene substituted with 1 to 8 deuteriums, toluene substituted with 1 to 8 deuteriums, and xylene substituted with 1 to 10 deuteriums, etc., but is not limited thereto, and specifically, may be selected from structures below:

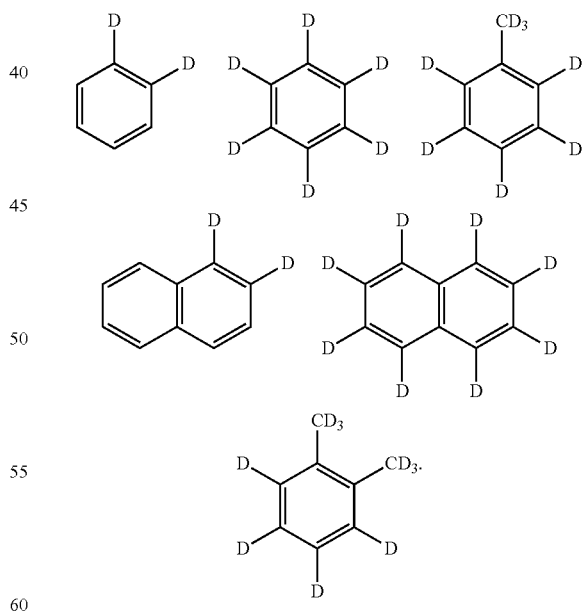

In an exemplary embodiment of the present invention, the C2-C30 unsaturated hydrocarbon substituted with at least one deuterium may be selected from structures below, but is not limited thereto:

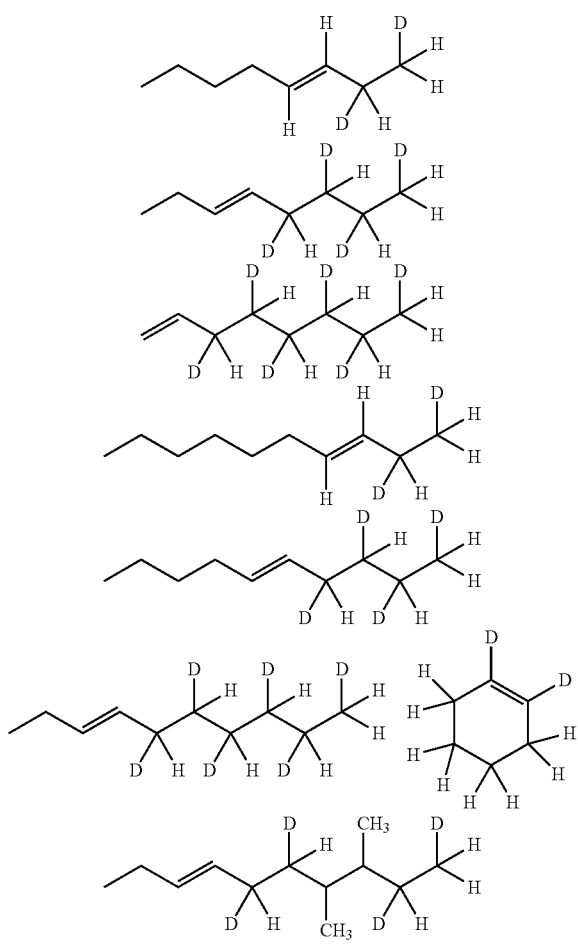

As an example, among the saturated hydrocarbons configuring the oil products, that is, fuel oil, a gasoline component is a $C_4$-$C_{12}$ material, a kerosene component is a $C_9$-$C_{15}$ material, and a diesel component is a $C_{10}$-$C_{30}$ material. Some of the hydrogens in specific saturated hydrocarbons of the respective components of fuel oil may be substituted with deuterium. A natural amount of deuterium is 0.015%, and possibility that two or more deuteriums practically present in one molecule of the saturated hydrocarbon configuring the oil is extremely low, and thus, two or more hydrogens in the saturated hydrocarbon configuring the fuel may be artificially substituted with the deuterium. The saturated hydrocarbon substituted with the deuterium has minimal differences from the conventional saturated hydrocarbon configuring the oil products in view of a molecular weight and polarity, and thus, there are no large differences in view of physical and chemical properties.

Accordingly, the marker for oil products used in the present invention has a structure in which one or more of hydrogens of the conventional oil components are substituted with deuterium(s), wherein a change in molecular weight and a polarity degree are not large. The marker for oil products has high solubility in oil fuels and a liquid form, and neither has color nor has a change in a fuel shape even if the marker is added to the oil fuels. Accordingly, the illegal removal of the marker is virtually impossible due to physical and chemical similarity with the conventional oil components. In addition, it is able to determine whether the marker of the present invention is contained by using simple measurement apparatuses, which makes it possible to easily determine whether the illegal incorporation of the oil products occurs.

A process of producing the marker for oil products used in the present invention is shown in Reaction Schemes 1 to 4 below, but is not limited thereto. In addition, positions of double bonds in starting materials are not limited, and the deuterium may be present inside of the hydrocarbon or at the end of the hydrocarbon depending on the positions of double bonds.

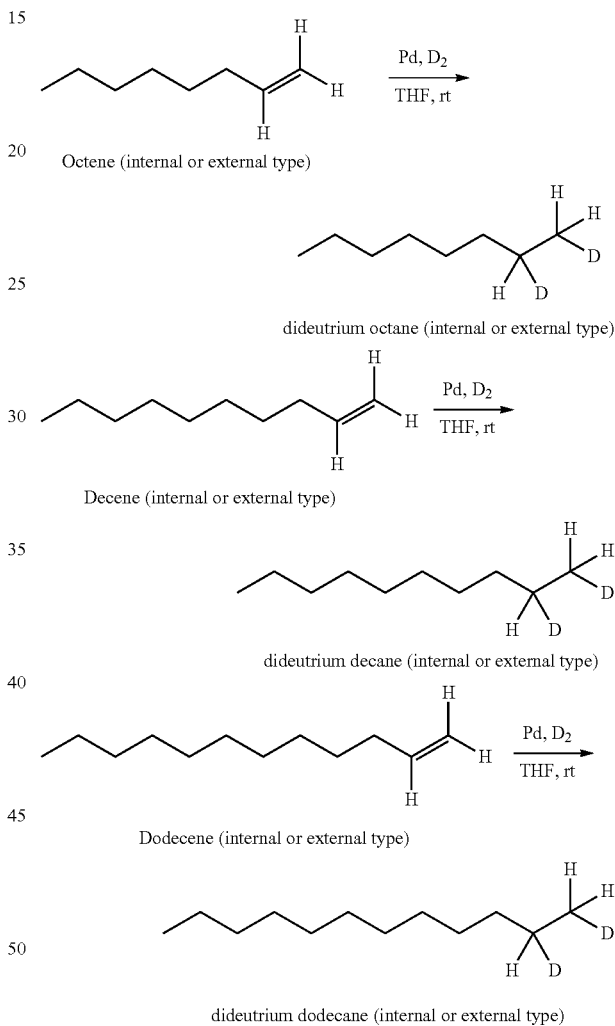

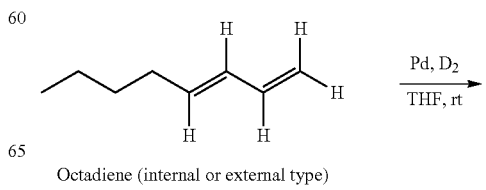

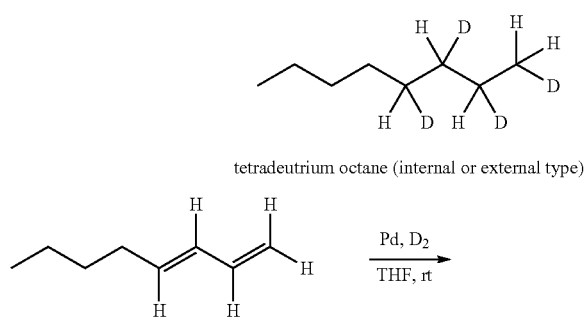
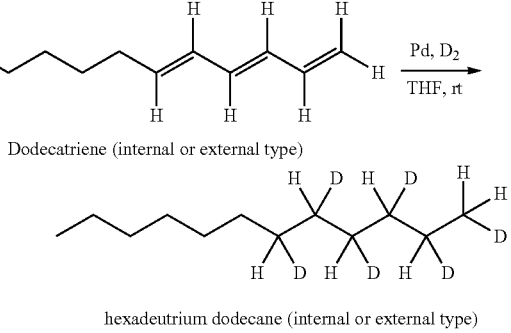
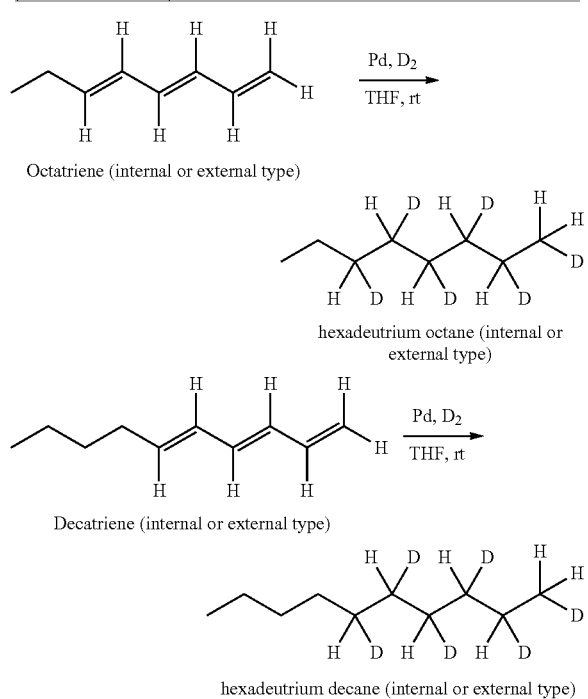

[Reaction Scheme 3] Production of marker substituted with six deuteriums.

[Reaction Scheme 4] Production of marker substituted with one deuterium.

In an exemplary embodiment of the present invention, more preferably, the method for marking oil products may include: measuring a gas chromatography mass analysis spectrum of the oil product labeled with the marker for oil products, the marker including aromatic hydrocarbon substituted with at least one deuterium or saturated hydrocarbon substituted with at least one deuterium.

In addition, the present invention provides a marker composition for oil products including hydrocarbon substituted with at least one deuterium.

In an exemplary embodiment of the present invention, the hydrocarbon may be one or more selected from C1-C30 saturated hydrocarbon substituted with at least one deuterium, C5-C30 aromatic hydrocarbon substituted with at least one deuterium, and C2-C30 unsaturated hydrocarbon substituted with at least one deuterium.

The marker composition for oil products according to the present invention includes hydrocarbon substituted with at least one deuterium as the marker, which has no change in the marker over time which is different from the conventional marker for oil products, and thus, there is no problem of reducing marking function. Further, it is possible to easily mark the oil products using the nuclear magnetic resonance spectroscopy or the gas chromatography mass analysis spectrometry, thereby making it possible to prevent illegal distribution and use of similar gasoline and similar oil products.

The marker composition for oil products may be used for markers for oil products such as gasoline, diesel, heavy oil, kerosene, biodiesel, bioethanol, and an organic solvents such as xylene, toluene, benzene, etc., and more preferably, gasoline, diesel, heavy oil, kerosene, etc.

In an exemplary embodiment of the present invention, the marker composition for oil products may further include a chemical marker, a visible marker, or a mixture thereof.

The visible marker refers to a color form of marker, and has a low price, but is easily removed by decoloration, and the chemical marker refers to a marker that analyzes absorbance of specific wavelength of a material formed by a chemical reaction with the marker, using a UV-Vis spectrophotometer.

In an exemplary embodiment of the present invention, the chemical marker may be Unimark 1494DB, and the visible marker may be one or two or more selected from MAXOL RED-4L, GREENER, MAXOL BLUE-4L, MAXOL BLACK, etc.

In an exemplary embodiment of the present invention, the marker composition for oil products may include the deuterium marker, and the chemical marker, the visible marker or a mixture thereof at a concentration ratio of 1:0.1 to 1:1. Within the above-described range, it is able to compensate the disadvantages of the conventional markers to easily determine whether the illegal mixing of the oil products occurs.

Hereinafter, the present invention is described in more detail through exemplary embodiments, but these exemplary embodiments are only provided for the purpose of description, and should not be construed as limiting the present invention.

In order to synthesize the deuterium-substituted marker for fuel having similar physical and chemical properties to those of a component configuring the oil product, $C_8$ unsaturated hydrocarbon including olefin was selected as the gasoline component, $C_{10}$ unsaturated hydrocarbon including olefin was selected as the kerosene component, and $C_{12}$ unsaturated hydrocarbon including olefin was selected as the diesel component, followed by deuteration (hydrogenation) reaction using deuterium gas ($D_2$ gas) or deuterium hydride gas (DH gas), Pd/C or Rh/C was used as a catalyst.

PRODUCTION EXAMPLE 1

Production of 2,3-dideuterium octane

2-Octene (5 g, 1 eq) was charged in 100 mL round bottom flask, and anhydrous tetrahydrofuran (THF) (30 mL) was added thereto, and a palladium catalyst Pd/C (237 mg, 0.05 eq) was added thereto. The flask was filled with $D_2$ gas, and reacted at room temperature. Termination of the reaction was confirmed by $^1$H-NMR. After the termination of the reaction, water (30 mL) was added, and the reaction product was extracted with ether, and moisture was removed by anhydrous $MgSO_4$, followed by concentration via rotary evaporator. The concentrated residues were purified by column chromatography (Hexane:EtOAc=15:1) to obtain 2,3-dideuterium octane in a colorless liquid form (4.87 g, yield of 94%) as a title compound. The product was structurally analyzed by $^1$H-NMR and $^{13}$C-NMR and FT-IR.

$^1$H-NMR (400 MHz, $CDCl_3$) δ 1.26 (m, 11H), 0.88 (m, 5H); $^{13}$C-NMR (100 MHz, $CDCl_3$) δ 32.15, 29.54, 22.88, 14.16; FT-IR ($cm^{-1}$) 2969, 2928, 2875, 2867, 1468, 1457, 1379.

PRODUCTION EXAMPLE 2

Production of Mixture of 2-deuterium Octane and 3-deuterium Octane

2-Octene (5 g, 1 eq) was charged in 100 mL round bottom flask, and anhydrous tetrahydrofuran (THF) (30 mL) was added thereto, and a palladium catalyst Pd/C (237 mg, 0.05 eq) was added thereto. The flask was filled with DH gas, and reacted at room temperature. Termination of the reaction was confirmed by $^1$H-NMR. After the termination of the reaction, water (30 mL) was added, and the reaction product was extracted with ether, and moisture was removed by anhydrous $MgSO_4$, followed by concentration via rotary evaporator. The concentrated residues were purified by column chromatography (Hexane:EtOAc=15:1) to obtain the mixture of 2-dideuterium octane and 3-deuterium octane in a colorless liquid form (4.72 g, yield of 92%) as a title compound. The product was structurally analyzed by $^1$H-NMR and $^{13}$C-NMR and FT-IR.

$^1$H-NMR (400 MHz, $CDCl_3$) δ 1.26 (m, 11H), 0.88 (m, 5H); $^{13}$C-NMR (100 MHz, $CDCl_3$) δ 32.15, 29.54, 22.88, 14.16; FT-IR ($cm^{-1}$) 2969, 2928, 2875, 2867, 1468, 1457, 1379.

PRODUCTION EXAMPLE 3

Production of 2,3-dideuterium Decane

2-Decene (5 g, 1 eq) was charged in 100 mL round bottom flask, and anhydrous tetrahydrofuran (THF) (30 mL) was added thereto, and a palladium catalyst Pd/C (190 mg, 0.05 eq) was added thereto. The flask was filled with $D_2$ gas, and reacted at room temperature. Termination of the reaction was confirmed by $^1$H-NMR. After the termination of the reaction, water (30 mL) was added, and the reaction product was extracted with ether, and moisture was removed by anhydrous $MgSO_4$, followed by concentration via rotary evaporator. The concentrated residues were purified by column chromatography (Hexane:EtOAc=15.1) to obtain 2,3-dideuterium decane in a colorless liquid form (4.73 g, yield of 92%) as a title compound. The product was structurally analyzed by $^1$H-NMR and $^{13}$C-NMR and FT-IR.

$^1$H-NMR (400 MHz, $CDCl_3$) δ 1.39 (m, 3H), 1.26 (m, 11H), 0.88 (m, 6H); $^{13}$C-NMR (100 MHz, $CDCl_3$) δ 32.16, 29.89, 29.59, 22.88, 14.16; FT-IR ($cm^{-1}$) 2969, 2927, 2873, 2866, 1468, 1456, 1379.

PRODUCTION EXAMPLE 4

Production of 2,3-dideuterium Dodecane

2-Dodecene (5 g, 1 eq) was charged in 100 mL round bottom flask, and anhydrous tetrahydrofuran (THF) (30 mL) was added thereto, and a palladium catalyst Pd/C (158 mg, 0.05 eq) was added thereto. The flask was filled with $D_2$ gas, and reacted at room temperature. Termination of the reaction was confirmed by $^1$H-NMR. After the termination of the reaction, water (30 mL) was added, and the reaction product was extracted with ether, and moisture was removed by anhydrous $MgSO_4$, followed by concentration via rotary evaporator. The concentrated residues were purified by column chromatography (Hexane:EtOAc=15:1) to obtain 2,3-dideuterium dodecane in a colorless liquid form (4.88 g, yield of 95%) as a title compound. The product was structurally analyzed by $^1$H-NMR and $^{13}$C-NMR and FT-IR.

$^1$H-NMR (400 MHz, $CDCl_3$) δ 1.27 (m, 18H), 0.88 (m, 6H); $^{13}$C-NMR (100 MHz, $CDCl_3$) δ 32.13, 29.87, 29.56, 22.85, 14.14; FT-IR ($cm^{-1}$) 2968, 2925, 2873, 2866, 1468, 1378, 1342.

EXAMPLE 1

Analysis of Marker in Kerosene

The deuterium-substituted marker for oil is able to be analyzed by D-NMR, but since GC-MS has a high detection limit, an additive for oil developed in the present invention was analyzed by using the GC-MS.

10 ppm of a benzene D-6 ($C_6D_6$) marker of the present invention was added to a domestically distributed kerosene product, and then, whether the marker was present was determined by using the GC-MS.

MD-GCMS (Shimadzu, Japan) consisting of Shimadzu GC-2010 Plus and GCMS-QP2010 Ultra was utilized as GC-MS equipment used for the present analysis. In order to improve separation and analysis capabilities, marker parts were selectively delivered to a secondary column, and information on m/z=84 corresponding to a molecular weight of the benzene D-6 ($C_6D_6$) marker was obtained using SIM (selective ion mode). A primary column was 100% dimethylpolysiloxane column, and the secondary column was (5%-phenyl)-methylpolysiloxane column. For primary separation, the product was maintained in an oven under temperature condition for 1 minute at 100° C., and then, the temperature was raised at 20° C./min up to 320° C., and the product was maintained for 15 minutes at 320° C. For secondary separation analysis, the product was maintained in an oven under temperature condition for 7 minutes at 50° C., and then, the temperature was raised at 5° C./min up to 150° C., and total analysis time was set to be 27 minutes. A sample injection condition was 1 μL, and a split ratio was set to be 50:1. Results thereof were illustrated in FIG. 1.

As illustrated in FIG. 1, it was confirmed that the benzene D-6 ($C_6D_6$) marker was selectively detected at 6.25 minutes.

EXAMPLE 2

Analysis of Whether the Marker was Detected in the Mixture Including Kerosene Mixed with the Marker and Diesel The kerosene including 10 ppm of benzene D-6 ($C_6D_6$) marker of Example 1 was illegally mixed with a normal diesel at a volume ratio of 1:1, and then, whether the marker was selectively detected was analyzed by using the GC-MS under the same condition as Example 1. Results thereof were illustrated in FIG. 2.

Figure 2:
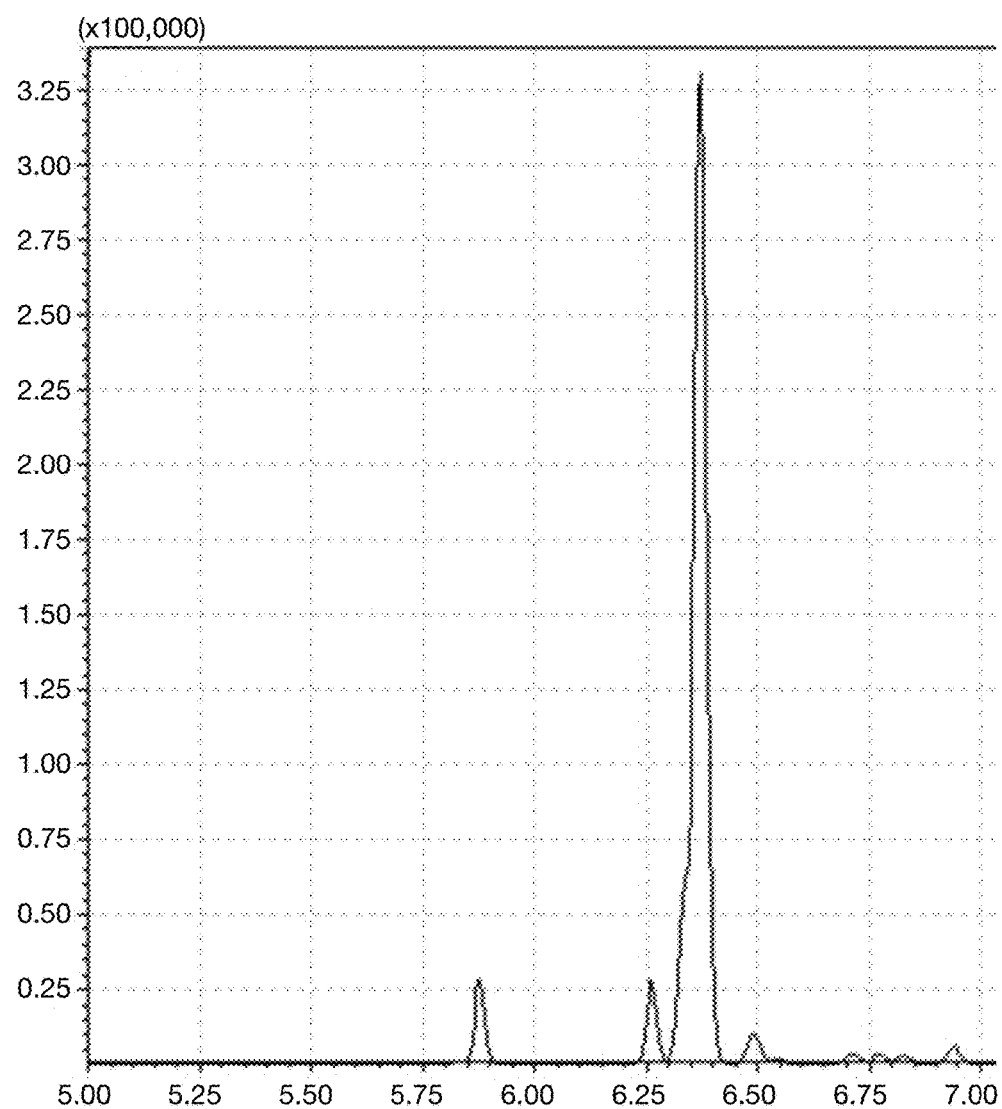
FIG. 2 illustrates GC-MS spectrum of a mixture in which the kerosene mixed with the benzene D-6 ($C_6D_6$) marker is mixed with diesel.

As illustrated in FIG. 2, the benzene D-6 ($C_6D_6$) which is the marker included in the kerosene was selectively detected at 6.25 minutes, such that it was confirmed that the kerosene was incorporated in the diesel.

EXAMPLE 3

Analysis I of Whether the Marker was Removed in the Mixture Including Kerosene Mixed with the Marker and Diesel In order to confirm whether the illegal removal occurred which is the problem of the conventional marker, the kerosene including 10 ppm of benzene D-6 ($C_6D_6$) marker of Example 1 was mixed with a normal diesel at a volume ratio of 1:1, and zeolite (Duksan Science, granular 5~8 mesh) passed therethrough, and then, whether the removal of the marker occurred was confirmed by using the GC-MS in the same method as Example 1. Results thereof were illustrated in FIG. 3.

Figure 3:
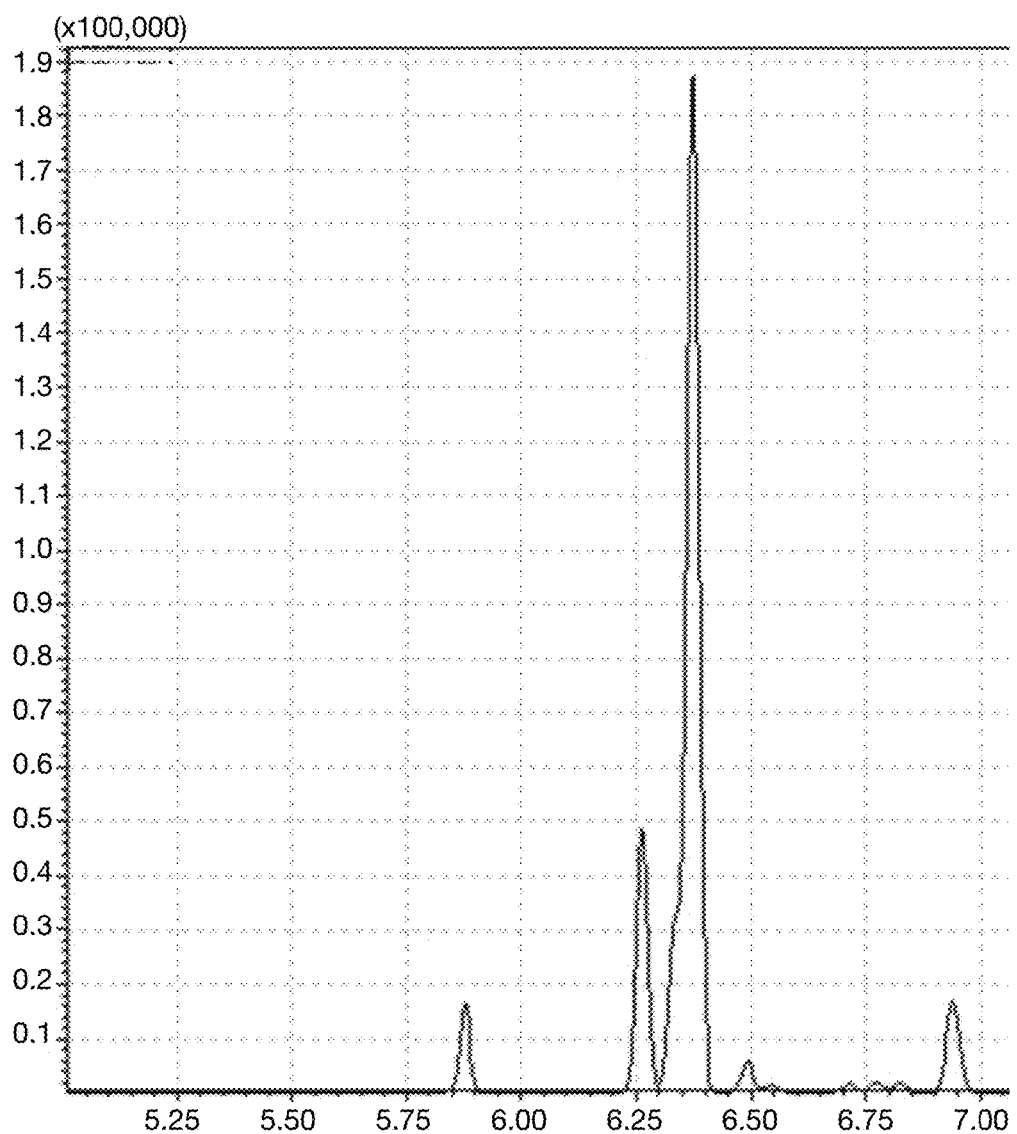
FIG. 3 illustrates GC-MS spectrum of a mixture in which the kerosene mixed with the benzene D-6 ($C_6D_6$) marker is mixed with diesel after treatment with Zeolite.

As illustrated in FIG. 3, the benzene D-6 ($C_6D_6$) marker was detected at 6.25 minutes without change in sensitivity, such that it could be appreciated that it was impossible to perform the illegal removal of the marker for oil products of the present invention.

EXAMPLE 4

Analysis II of Whether the Marker was Removed in the Mixture Including Kerosene Mixed with the Marker and Diesel In order to confirm whether the illegal removal occurred which is the problem of the conventional marker, the kerosene including 10 ppm of benzene D-6 ($C_6D_6$) marker of Example 1 was mixed with a normal diesel at a volume ratio of 1:1, and activated carbon passed therethrough, and then, whether the removal of the marker occurred was confirmed by using the GC-MS in the same method as Example 1. Results thereof were illustrated in FIG. 4.

Figure 4:
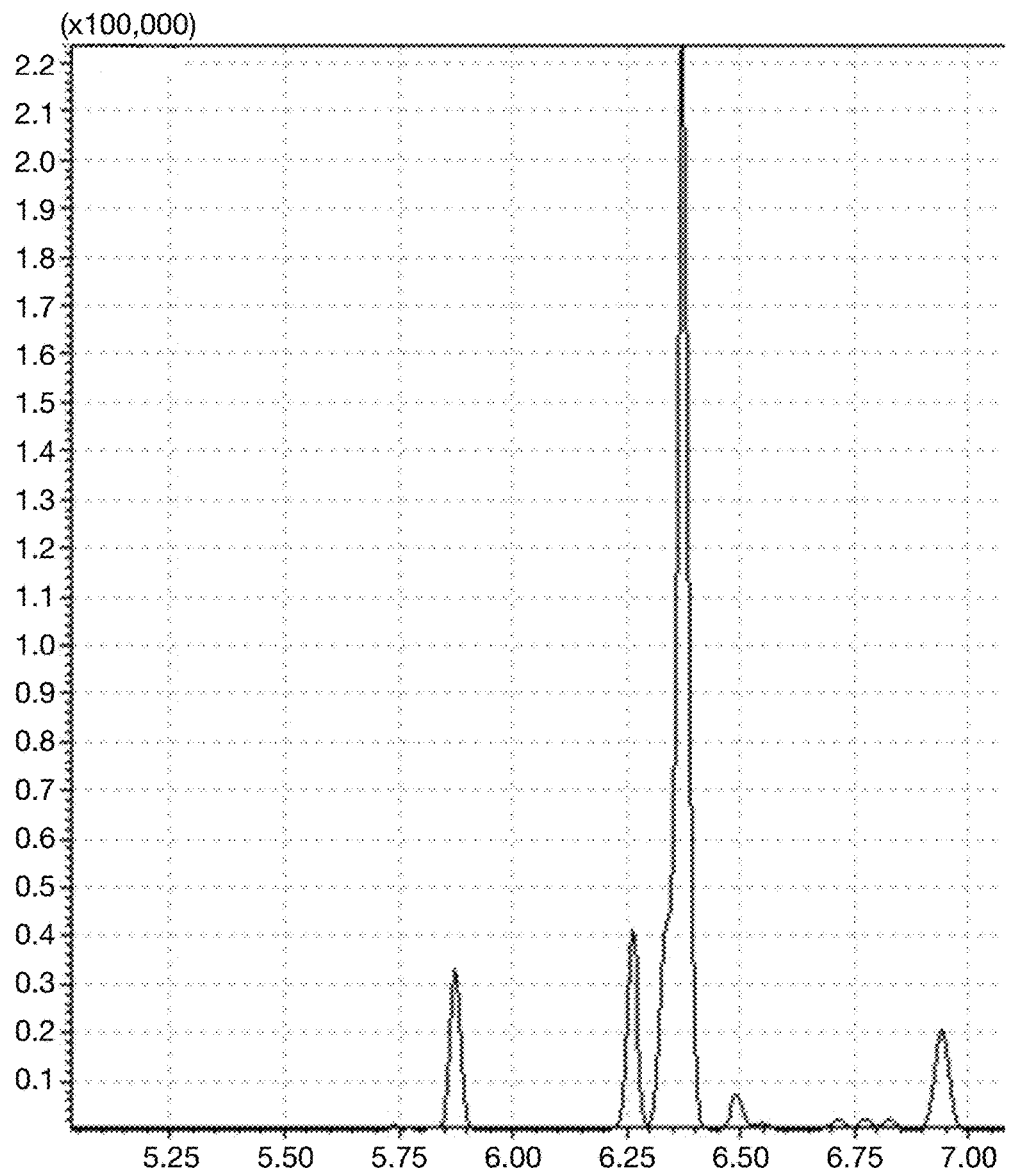
FIG. 4 illustrates GC-MS spectrum of a mixture in which the kerosene mixed with the benzene D-6 ($C_6D_6$) marker is mixed with diesel after treatment with activated carbon.

As illustrated in FIG. 4, the benzene D-6 ($C_6D_6$) marker was detected at 6.25 minutes without change in sensitivity, such that it could be appreciated that it was impossible to perform the illegal removal of the marker for oil products of the present invention.

EXAMPLE 5

Analysis of Marker in Kerosene 10 ppm of a 1,2-dideuterium decane ($C_{10}H_{22}D_2$) marker of the present invention was added to a domestically distributed kerosene product, and then, whether the marker was present was determined by using the GC-MS.

The equipment of Example 1 was utilized in the present analysis, information on m/z=144 corresponding to a molecular weight of the 1,2-dideuterium decane ($C_{10}H_{22}D_2$) marker was obtained using SIM (selective ion mode). The column to be used was the same as Example 1. For the primary separation, the product was maintained in an oven under temperature condition for 1 minute at 100° C., and then, the temperature was raised at 10° C./min up to 320° C., and the product was maintained for 7 minutes at 320° C. For secondary separation analysis, the product was maintained in an oven under temperature condition for 1 minute at 100° C., and then, the temperature was raised at 10° C./mins up to 320° C., and total analysis time was set to be 30 minutes. A sample injection condition was 1 μL, and a split ratio was set to be 50:1.

As a result, it was confirmed that the 1,2-dideuterium decane ($C_{10}H_{22}D_2$) marker was selectively detected at 7.8 minutes.

EXAMPLE 6

Analysis of Whether Marker was Detected in the Mixture Including Kerosene Mixed with the Marker and Diesel The kerosene including 10 ppm of 1,2-dideuterium decane ($C_{10}H_{22}D_2$) marker of Example 5 was illegally mixed with a normal diesel at a volume ratio of 1:3, and then, whether the marker was selectively detected was analyzed by using the GC-MS under the same condition as Example 1.

As a result, the 1,2-dideuterium decane ($C_{10}H_{22}D_2$) which is the marker included in the kerosene was selectively detected at 7.8 minutes, such that it was confirmed that the kerosene was incorporated in the diesel.

EXAMPLE 7

Analysis of Marker in Kerosene Mixed with Various Deuterium Markers 1,2-Dideuterium decane ($C_{10}H_{22}D_2$), benzene D-6 ($C_6D_6$), toluene D-8 ($C_7D_8$), cyclohexane D-12 ($C_6D_{12}$) each having a concentration of 10 ppm according to the present invention was added to a domestically distributed kerosene product, and then, whether the marker was present was determined by using the GC-MS.

As analysis results, the respective materials obtained m/z values corresponding to the molecular weights of the corresponding deuterium compounds at a specific retention time, and thus, qualitative and quantitative analysis could be performed, and whether the marker was present could be easily confirmed.

EXAMPLE 8

Analysis of Marker in Kerosene Mixed with Deuterium Marker and Chemical Marker

The deuterium marker of the present invention and the chemical marker each having a concentration of 10 ppm were added to a normal kerosene, and then, confirming whether the marker was present. 1,2-Dideuterium decane ($C_{10}H_{22}D_2$) was used as the deuterium marker, and Unimark 1494DB was used as the chemical marker.

The deuterium marker was analyzed in the same method as Example 1 by using the GC-MS. As the analysis results, it was observed that the deuterium marker, i.e., the 1,2-dideuterium decane ($C_{10}H_{22}D_2$) had m/z values corresponding to the molecular weight of the corresponding deuterium compound at a specific retention time of 7.9 minutes. Accordingly, it could be appreciated that even though the different kind of marker in addition to the deuterium marker was mixed, it was able to easily confirm the deuterium marker using the GC-MS.

The chemical marker, i.e., the Unimark 1494DB was color-developed with Unimark 1494DB Developer C-5, and analyzed by using UV-VIS. The chemical marker, i.e., Unimark 1494DB was color-developed to be purple by adding Unimark 1494DB Developer C-5. As UV-VIS analysis results, it could be appreciated that the conventional chemical marker, i.e., the Unimark 1494DB was selectively detected at the maximum absorption wavelength of the chemical marker, Unimark 1494DB. In addition, it could be visually confirmed that the chemical marker, i.e., the Unimark 1494DB was color-developed to be purple.

Therefore, it was able to easily and visually recognize whether the chemical marker was present in a field, and to analyze the deuterium in a laboratory, thereby compensating the disadvantages of the chemical marker and the covert marker, and actively utilizing the advantages thereof.

INDUSTRIAL APPLICABILITY

The present invention provides a novel form of a marker for oil products which is not easily removable by physical and chemical methods and is able to easily determine whether illegal mixing of the oil products occurs, which is able to easily determine whether illegal incorporation of the fuel occurs, by labeling oil products with the marker using hydrocarbon substituted with at least one deuterium, and by determining whether the deuterium-substituted marker for fuel is contained by nuclear magnetic resonance spectroscopy or gas chromatography mass spectrometry.

In addition, the marker for oil products according to the present invention has a structure in which hydrogen of the conventional oil components is substituted with deuterium, wherein a change in molecular weight and a polarity degree are not large. The marker for oil products has high solubility in oil fuels, and a liquid form, and neither has colors nor has a change in a fuel shape even if the marker is added to the oil fuels. Accordingly, the illegal removal of the marker is virtually impossible due to physical and chemical similarity with the conventional oil components.

The invention claimed is:
1. A method for marking oil products comprising:
measuring a gas chromatography mass analysis spectrum of an oil product labeled with a marker for oil products, the marker including hydrocarbon substituted with at least one deuterium selected from structures below:

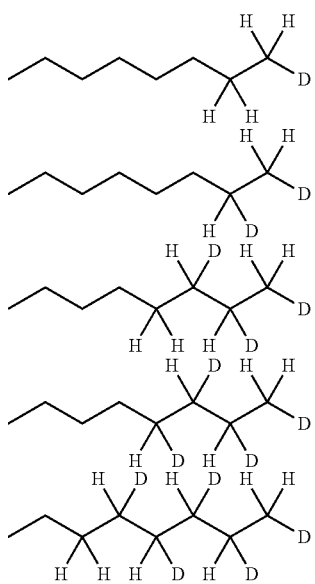

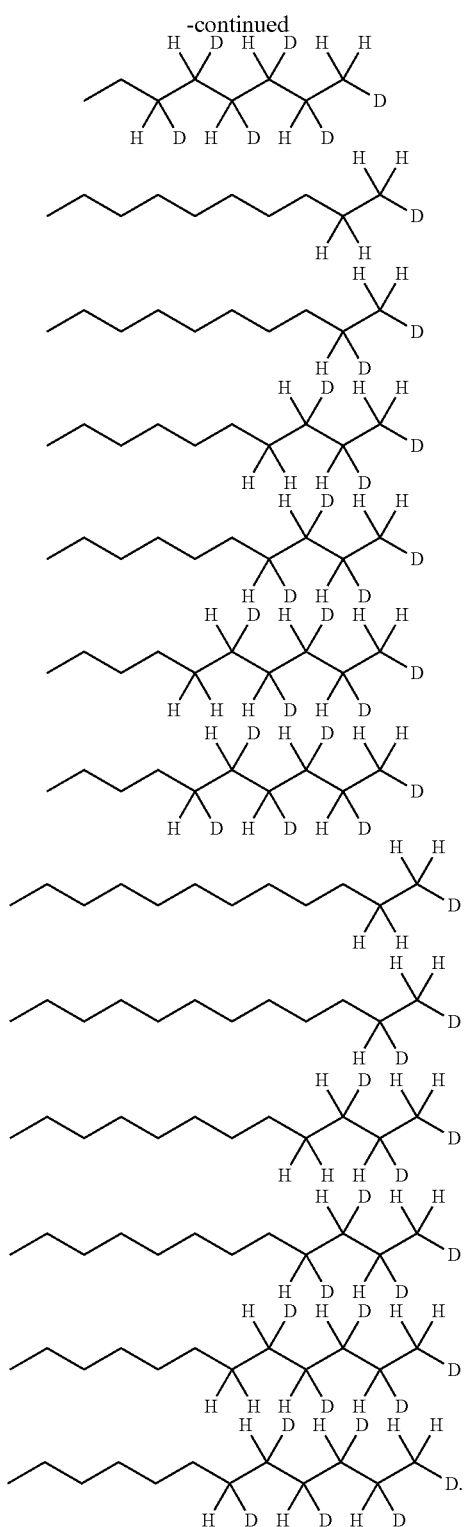
cyclohexane D-12 (C$_6$D$_{12}$)
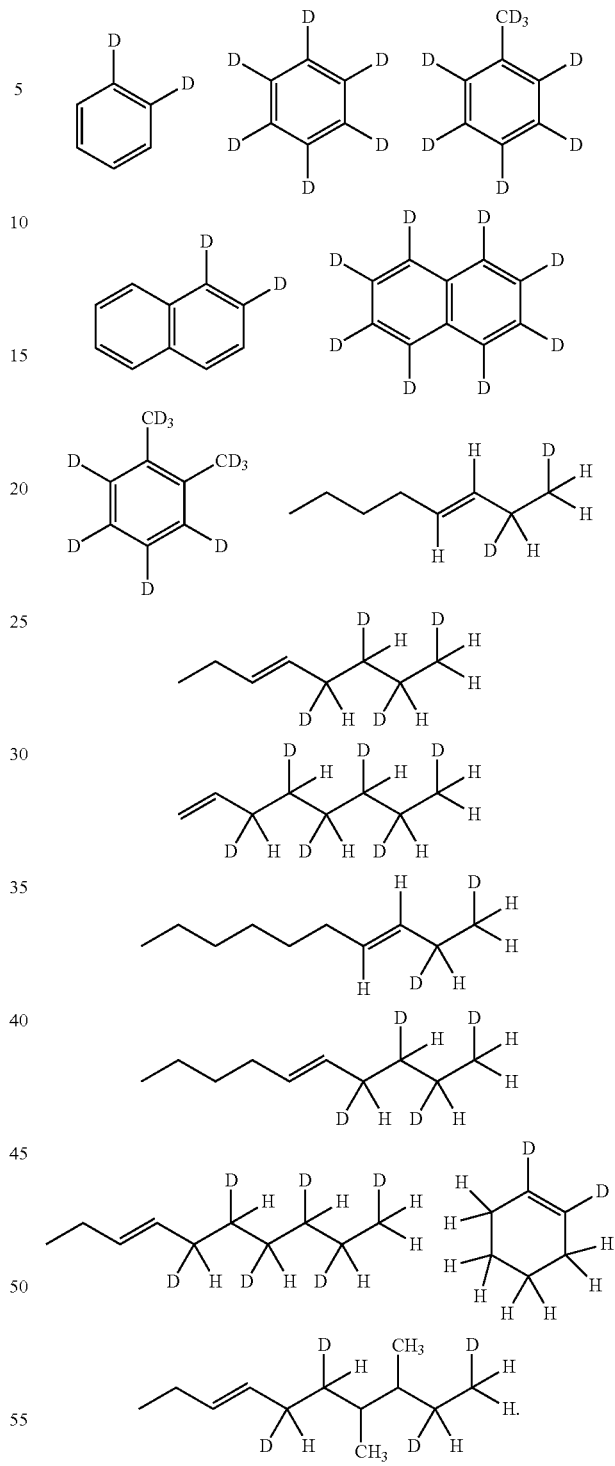
* * * * *